United States Patent [19]

von Strandtmann et al.

[11] 4,116,971
[45] Sep. 26, 1978

[54] 3-(1H-TETRAZOL-5-YL)CHROMONES

[75] Inventors: Max von Strandtmann, New Castle, Del.; Marvin P. Cohen, New Milford, N.J.; Sylvester Klutchko, Ann Arbor, Mich.; John Shavel, Jr., Mendham, N.J.

[73] Assignee: Warner-Lambert Company, Morris Plains, N.J.

[21] Appl. No.: 824,385

[22] Filed: Aug. 15, 1977

[51] Int. Cl.$^2$ .................... G07D 257/04; D61K 31/41
[52] U.S. Cl. .................... 260/308 D; 424/269
[58] Field of Search .................... 260/308 D

[56] References Cited

U.S. PATENT DOCUMENTS

| | | | |
|---|---|---|---|
| 3,862,143 | 1/1975 | Klutchko et al. | 260/345.2 |
| 3,896,114 | 7/1975 | Nohara et al. | 260/308 D X |

FOREIGN PATENT DOCUMENTS 2,523,194  12/1975  Fed. Rep. of Germany ........ 260/345.2

*Primary Examiner*—Paul M. Coughlan, Jr.
*Assistant Examiner*—D. B. Springer
*Attorney, Agent, or Firm*—Albert H. Graddis; Frank S. Chow

[57] ABSTRACT

There is described 3-(1H-tetrazol-5-yl)chromones having the following structural formula:

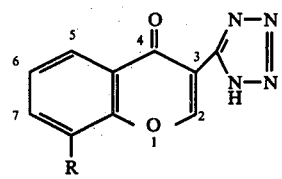

in which R is lower alkoxy having 1 to 3 carbon atoms, aryl such as phenyl, halogen or trihalo lower alkyl. These compounds exhibit anti-allergic properties and are indicated in the treatment of allergic conditions such as hay fever and asthma.

3 Claims, No Drawings

3-(1H-TETRAZOL-5-YL)CHROMONES

BACKGROUND OF THE INVENTION

1. Field of the Invention

The present invention relates to 3-(1H-tetrazol-5-yl) chromones having the following structural formula:

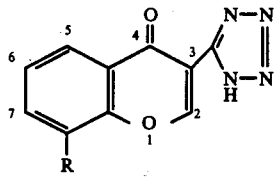

in which R is lower alkoxy having 1 to 3 carbon atoms, aryl such as phenyl, halogen or trihalo lower alkyl. These compounds are useful as anti-allergic agents.

2. Description of the Prior Art

It is known that compounds having a chromone nucleus exhibit oral anti-allergic properties. See, for example, our French Pat. No. 2,124,427 published Mar. 2, 1972. Also, it is know that 3-substituted chromones exhibit anti-allergic activity. In addition, in U.S. Pat. No. 3,896,114 there are described, inter alia, 6-ethyl, 6-methoxy, 6-chloro and the unsubstituted 3-(1H-tetrazol-5-yl) chromones, as having such anti-allergic properties.

DESCRIPTION OF THE INVENTION

We have found that the compounds of the present invention, particularly the 8-lower alkoxy compounds, possess biological properties that were superior to any of the previously known compounds in the chromone class as will become evident from the following description. Thus, a side-by-side comparison has been made between 3-(1H-tetrazol-5-yl)-8-methoxy chromone, a compound of the present invention, and 3-(1H-tetrazol-5-yl)-6-methoxy chromone, a compound described in U.S. Pat. No. 3,896,114 of their ability to inhibit passive cutaneous anaphylaxis (PCA). This is described by I. Mota, in *Life Sciences*, 7, 465 (1964), Z. Ovary and O. Bier, *Proc. Soc. Exptl. Biol. Med.*, 81, 584 (1952) and D. J. Herzig, et al., *Immunopharmacology* (Spectrum Publications, N.Y., 1975) pp. 103–125. The results of this test were as follows:

Administration of 3-(1H-tetrazol-5-yl)-8-methoxy chromone to rats by oral route of 0.1 mg/kg dose level caused 100% inhibition of PCA. Administration of 3-(1H-tetrazol-5-yl) -6-methoxy chromone under identical conditions caused no inhibition.

In a set of separate tests, the oral $ID_{50}$, which is the dose causing 50% inhibition of PCA, of 3-(1H-tetrazol-5-yl)-8-methoxy chromone was found to be in the range of 12 micrograms. This suggests that the compounds of the present invention are 18 times more potent than said 6-methoxy substituted compound.

On the other hand, the isomeric 2-(1H-tetrazol-5-yl)chromone derivatives were also studied and found to be orally inactive. These isomeric 2-(1H-tetrazol-5-yl)chromone derivatives are described in German Offenlegungsschrift No. 2,105,191.

In view of the above, the compounds of the present invention are particularly suitable for the management of allergic conditions such as hay fever and asthma. Generally speaking, a dose of 0.012 to 0.100 mg/kg orally or by aerosol administration is suggested for the relief of such allergic conditions. Accordingly, the present invention also includes within its scope methods for the treatment of asthmatic conditions by the administration of the compounds of this invention.

According to a feature of the present invention, the above compounds are prepared by refluxing R-substituted 4-oxo-4H-1-benzopyran-3-carbonitrile in tetrahydrofuran with aluminum chloride and sodium azide. The starting compound is covered in Warner-Lambert's U.S. Pat. No. 3,862,143 (1975) and the process for its production in U.S. Pat. No. 3,853,921 (1974).

The invention includes within its scope pharmaceutical compositions which comprise at least one compound of formula I, together with a pharmaceutical carrier or coating. In clinical practice, the novel compounds of the present invention will normally be administered orally.

Solid compositions for oral administration include compressed tablets, pills, dispersible powders and granules. In such solid compositions, one or more of the active compounds is, or are, admixed with at least one inert diluent such as calcium carbonate, potato starch, alginic acid or lactose. The compositions may also comprise, as is normal practice, additional substances other than inert diluents, e.g., lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

The compounds of the invention may be administered orally by inhalation. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. The solution may contain stabilizing agents such as sodium bisulphite and buffering agents to give it an isotonic character, e.g., sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form the active ingredients in pharmaceutically-acceptable solvents, e.g., ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g., metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

To further illustrate the practice of this invention, the following examples are included:

EXAMPLE 1

8-Methoxy-4-oxo-4H-1-benzopyran-3-carbonitrile. A mixture of 5.2 g (0.026 mole) of 8-methoxy-4-oxo-4H-1-benzopyran-3-carboxaldehyde, 2.08 g (0.03 mole) of hydroxylamine hydrochloride and 75 ml of 97% formic acid was heated with stirring until all solid dissolved (T=60° C.). A quantity of 3.4 g (0.05 mole) of sodium formate was added. The resulting slurry was heated to reflux. After 15 minutes all solid was in solution. After 3 hours of reflux the solution was cooled, water (300 ml) was added and the separated solid was filtered, washed with water and dried; wt. 3.6 g (68%); m.p. 225°–230°. Recrystallization from tetrahydrofuran gave pure nitrile; m.p. 232°–234°.

Anal. Calcd. for $C_{11}H_7NO_3$: C, 65.67; H, 3.51; N, 696. Found: C, 65.71; H, 3.48; N, 7.05.

EXAMPLE 2

8-Methoxy-3-(1H-tetrazol-5-yl)-4H-1-benzopyran-4-one. A mixture of 125ml of tetrahydrofuran, 6 g of $AlCl_3$, 11.6 g of $NaN_3$ and 8.04 g of 8-methoxy-4-oxo-4H-1-benzopyran-3-carbonitrile prepared as described in Example 1, was refluxed for 24 hours under a stream of nitrogen. The mixture was cooled and treated with 60 ml of concentrated HCl. The solvent was evaporated under reduced pressure, and the residue was filtered, washed with cold water and recrystallized from dimethylformide, yielding the above compound. Yield, 3.5 g (35%).

The characteristics of this compound are: m.p. 300–302°; $\lambda_{max}$ mµ (ε) 210 (18,800), 235 (20,900), 293 (5,550); $\lambda_{max}$ 770 (m), 880 (m), 920 (m), 1055 (s), 1155 (m), 1215 (m), 1290 (ms), 1585 (s), 1645 (s), 3220 (ms) $cm^{-1}$.

Anal. Calcd for $C_{11}H_8N_4O_3$: C, 54.10; H, 3.30; N, 22.94. Found: C, 53.84; H, 3.56; N, 23.01.

We claim:

1. A compound of the formula:

wherein R is lower alkoxy of 1 to 3 carbon atoms.

2. A compound according to claim 1 in which R is methoxy or ethoxy.

3. A compound according to claim 1 which is 8-methoxy-3-(1H-tetrazol-5-yl)-4H-1-benzopyran-4-one.